(12) United States Patent
Tehim et al.

(10) Patent No.: US 7,291,629 B2
(45) Date of Patent: Nov. 6, 2007

(54) NEUROTROPHIN ANTAGONIST COMPOSITIONS

(75) Inventors: Ashok Tehim, Ridgewood, NJ (US); Xiannong Chen, Alpharetta, GA (US)

(73) Assignee: Painceptor Pharma Corporation, Montreal, Quebec (CA)

( * ) Notice: Subject to any disclaimer, the term of this patent is extended or adjusted under 35 U.S.C. 154(b) by 0 days.

(21) Appl. No.: 11/179,610

(22) Filed: Jul. 13, 2005

(65) Prior Publication Data

US 2005/0250807 A1 Nov. 10, 2005

Related U.S. Application Data

(60) Division of application No. 09/758,917, filed on Jan. 11, 2001, now abandoned, which is a continuation of application No. 09/592,015, filed on Jun. 12, 2000, now abandoned, which is a continuation of application No. 09/440,505, filed on Nov. 15, 1999, now abandoned, which is a continuation of application No. 09/292,458, filed on Apr. 15, 1999, now abandoned, which is a continuation of application No. PCT/CA97/00779, filed on Oct. 20, 1997.

(30) Foreign Application Priority Data

Oct. 21, 1996 (GB) .................................. 9621902.7
May 27, 1997 (GB) .................................. 9710904.5

(51) Int. Cl.
*A61K 31/463* (2006.01)
*C07D 221/06* (2006.01)

(52) U.S. Cl. ........................................ 514/290; 546/79
(58) Field of Classification Search .................. 546/79; 514/290

See application file for complete search history.

(56) References Cited

U.S. PATENT DOCUMENTS

| | | | |
|---|---|---|---|
| 3,821,383 A | 6/1974 | Sestanj | 424/258 |
| 4,006,238 A | 2/1977 | Wade | |
| 4,204,063 A | 5/1980 | Brana | 546/99 |
| 4,254,109 A | 3/1981 | Sestanj | 424/178 |
| 4,874,863 A | 10/1989 | Brana | 540/99 |
| 5,076,831 A | 12/1991 | Saupe et al. | |
| 5,183,821 A | 2/1993 | Brana | 514/296 |
| 5,342,942 A | 8/1994 | Jaen et al. | 544/250 |
| 5,420,137 A | 5/1995 | Brana | 514/296 |
| 5,552,544 A | 9/1996 | Brana | 544/126 |
| 5,554,622 A | 9/1996 | Brana | 514/284 |
| 5,616,589 A | 4/1997 | Keilhauer et al. | 514/296 |
| 6,029,114 A | 2/2000 | Shamovsky et al. | |
| 6,291,247 B1 | 9/2001 | Riopelle et al. | |
| 6,300,331 B1 | 10/2001 | Noguchi et al. | |
| 6,468,990 B1 | 10/2002 | Ross et al. | |
| 6,492,380 B1 | 12/2002 | Ross et al. | |
| 7,148,352 B2 | 12/2006 | Ross et al. | |

FOREIGN PATENT DOCUMENTS

| | | |
|---|---|---|
| AU | 43963/09 | 1/2000 |
| DE | 2323555 A | 8/1974 |
| DE | 3707652 A1 | 9/1988 |
| EP | 0206322 A2 | 12/1986 |
| EP | 0 268 093 | 5/1988 |
| FR | 2521139 A | 8/1983 |

(Continued)

OTHER PUBLICATIONS

Neuron Abstract Vassilis et al 1993 Evidence that brain-derived neurotrophic factor is a trophic factor for motor neurons in vivo.*

(Continued)

*Primary Examiner*—Rita Desai
(74) *Attorney, Agent, or Firm*—Omar A. Nassif

(57) ABSTRACT

A pharmaceutical composition comprising a compound of Formula I

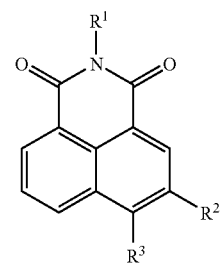

(I)

wherein $R^1$ is selected from, inter alia, alkyl, aryl-loweralkyl, heterocycle-loweralkyl, loweralkyl-carbonate; optionally substituted amino; benzimidaz-2-yl; optionally substituted phenyl; loweralkyl-$(R^5)(R^6)$ wherein one of $R^5$ and $R^6$ is selected from H and and the other is selected from carboxy, carboxy-loweralkyl and lower alkoxycarbonyl; $NHCH_2CH_2OX$ wherein X represents an in vivo hydrolyzable ester; and $R^2$ and $R^3$ are independently selected from H, $NO_2$, halo, di(loweralkyl)amino, cyano, C(O)OH, phenyl-S-, loweralkyl, and $Z(O)OR^7$ wherein Z is selected from C and S and $R^7$ is selected from H, lower alkylamino and arylamino; or pharmaceutically acceptable salts or certain in vivo hydrolyzable esters or amides thereof, in an amount effective to inhibit neurotrophin-mediated activity, and a suitable carrier, is described.

The compositions are useful to inhibit undesirable neurotrophin-mediated activity such as the neurite outgrowth that occurs in some neurodegenerative disease states.

1 Claim, No Drawings

FOREIGN PATENT DOCUMENTS

| | | |
|---|---|---|
| WO | WO98 17278 | 4/1998 |
| WO | WO98 34632 | 8/1998 |
| WO | WO98 52919 | 11/1998 |
| WO | WO 00 00472 | 1/2000 |

OTHER PUBLICATIONS

Katsuhiro et al. 1997. Antinociceptive Effects of Neurotrophin in a rat model of painful peripheral mononeuropathy.*

Brana, M.F., et al. "Enediynes as Antitumor Compounds: Synthesis of Tetrahydropyridine Derivatives," J. Org. Chem., 61: 1369-1374 (1996).

Brana, M.F., et al. "Synthesis and cytostatic activity of benz(de)isoquinolin-1,3-diones. Structure-activity relationships," Eur. J. Med. Chem-Chimica Therapeutica, 16(3): 207-212 (1981 (May-June).

Arient, J. and Marhan, J., "Imidazolfarbstoffe VI. Synthese und Eigenschaften des 1,2-Naphtholylenbenzimidazols," Collection Czechoslov. Chem. Commun. 26: 2774-2780 (1961).

Jaen, J.C. et al., "Kynurenic Acid Derivatives Inhibit the Binding of Nerve Growth Factor (NGF) to the Low-Affinity p75 NGF Receptor," J. Med. Chem. 38: 4439-4445 (1995).

Spiegel, K. et al., "PD 90780, A Non Peptide Inhibitor of Nerve Growth Factor's Binding to the P75 NGF Receptor," Biochemical and Biophysical Research Communications 217(2): 488-494 (Dec. 14, 1995).

Owolabi, J.B. et al., "Characterization of Antiallodynic Actions of ALE-0540, a Novel Nerve Growth Factor Receptor Antagonist, in the Rat," J. of Pharmacology and Experimental Therapeutics 289(3): 1271-1276 (1999).

Bailleux, V. et al., "Synthesis and Anticonvulsant Activity of Some N-Phenylphthalimides," Chem. Pharm. Bull. 42(9): 1817-1821 (1994).

Bailleux, V. et al., "Comparative Anticonvulsant Activity and Neurotoxicity of 4-Amino-N- (2,6-Dimethylphenyl) Phthalimide and Prototype Antiepileptic Drugs in Mice and Rats," Epilepsia 36(6): 559-565 (1995).

Bailleux, V. et al., "Anticonvulsant activity of some 4-amino-N-Phenylphthalimides and N- (3-amino-2-methylphenyl)phthalimides)," Biomed & Pharmacother 48: 95-101 (1994).

Shibata, Y. et al., "Phenylphthalimides with Tumor Necrosis Factor Alpha Production-Enhancing Activity," Chem. Pharm. Bull. 44(1): 156-162 (1996).

Chapman, J.M. et al., "Hypolipidemic Activity of Phthalimide Derivatives. 2. N-Phenylphthalimide and Derivatives," J. Med. Chem. 26: 237-243 (1983).

Chapman, J.M. et al., "Hypolipidemic Activity of Phthalimide Derivatives. 3. A Comparison of Phthalimide and 1,2-Benzisothiazolin-3-one 1,1-Dioxide Derivatives to Phthalimidine and 1,2-Benzisothiazoline 1,1-Dioxide Congeners." J. Med. Chem. 26: 243-246 (1983).

Chapman, J.M. et al., "Hypolipidemic Activity of Phthalimide Derivatives IV: Further Chemical Modification and Investigation of the Hypolipidemic Activity of N-Substituted Imides," J. Pharmaceutical Sciences 72(11): 1344-1347 (1983).

Chapman, J.M. et al., "Hypolipidemic Activity of Phthalimide Derivatives V: Reduced and Hydrolytic Products of Simple Cyclic Imides," J. Pharmaceutical Sciences 73(10): 1482-1484 (1984).

Tyman, J.H.P., "Fluorescent naphthalimide dyes," Chemical Abstract 108: 7506 (1997).

Maybridge—Online Catalogue Search Page (Jan. 8, 2001).

Ryan Scientific Inc. Online Search Page (Jan. 8, 2001).

Costi, M.P. et al., Eur J. Med. Chem. (1996) 31, 1011-1016.

Bundgaard H. (1985), Design of Prodrugs, Elsevier, Amsterdam-New York-Oxford, pp. 1-3, 27-28.

Information data sheet for PHG 01006, Ryan Scientific, Inc.

Kubinyi H. Die Pharmazie, (Oct. 1995) 50 (10) 647-62.

U.S. Appl. No. 11/525,841.

U.S. Appl. No. 11/627,129.

Chemical Abstracts 88:154305.

Laszlo Biczok et al., Phys. Chem. Chem. Phys. I: pp. 4759-4766 (Aug. 23, 1999).

Donker et al., "Synthesis and biological activities of aldose reducstase inhibitors bearing acyl benzensulfonamides as carboxylic acid surrogates", Eur. J. Med. Chem. 33: 15-22 (1998).

Donker et al., "Synthesis and biological activity of aldose reductase inhibitors with Michael acceptor substituents", Eur. J. Med. Chem. 34: 235-243 (1999).

Dubey et al., "A novel bifunctional fluorescent tag for use in molecular biology", Indian J. Chem. 34B: 876-878 (Oct. 1995).

Hodgkiss et al., "Fluorescent markers for hypoxic cells: a study of novel heterocyclic compounds that undergo bioreductive binding", Biochem. Pharmocol. 41: 533-541 (1991).

Hodgkiss et al., :Toxicity of 3-nitronaphthalimides to V79 379A Chinese hampster cells, Biochem. Pharmacol. 36: 1483-1487 (1987).

Szadowski et al., "Przemsyl Chemizny" 57(2): 70-74 (1978).

Nishizaki et al., "Infrared spectra of N-substittued naphthalimides", Nippon Kagaku Zasshi 86(7): 696-9 (1965) (Japan).

Lesauteur et al., "The Journal of Biochemistry", 1995, 270(12): 6564-69.

Gray et al., "Analytical Biochemistry", 1994, 216(1): 89-96.

* cited by examiner

NEUROTROPHIN ANTAGONIST COMPOSITIONS

RELATED APPLICATIONS

This application is a divisional of U.S. Ser. No. 09/758,917, filed Jan. 11, 2001 now abandoned, which is a continuation of U.S. Ser. No. 09/592,015, filed Jun. 12, 2000 now abandoned, which is a continuation of U.S. Ser. No. 09/440,505, filed Nov. 15, 1999 now abandoned, which is a continuation of U.S. Ser. No. 09/292,458, filed Apr. 15, 1999 now abandoned, which is a continuation of the U.S. designation of international application PCT/CA97/00779, filed Oct. 20, 1997, which claims priority to GB9710904.5, filed May 27, 1997, and GB9621902.7, filed Oct. 21, 1996, the entire teachings of which are incorporated herein by reference.

FIELD OF THE INVENTION

The present invention relates to neurotrophin antagonists. In particular, the present invention relates to compositions comprising an effective amount of a compound which inhibits or reduces undesirable neurotrophin activity, and a pharmaceutically acceptable carrier.

BACKGROUND OF THE INVENTION

A family of structurally and functionally related neurotrophic factors exist which are collectively known as neurotrophins. The family of neurotrophins includes the nerve growth factor (NGF), brain-derived neurotrophic factor (BDNF), neurotrophin-3 (NT-3), neurotrophin-4 (NT-4), neurotrophin-5 (NT-5) and neurotrophin-6 (NT-6).

The neurotrophins exhibit similar structural conformations, including three surface β-hairpin loops, a β-strand, an internal reverse turn region, and N- and C-termini. With respect to sequence similarities, the neurotrophins share approximately 50% amino acid identity. The neurotrophins are also functionally similar in that they each exhibit low affinity binding to a receptor known as the "p75 nerve growth factor receptor" or p75$^{NGFR}$. Each neurotrophin also exhibits binding to a receptor of the tyrosine kinase (trk) family which is of higher affinity than the binding to the p75 receptor. This interaction is believed to be related to neuron survival, but is also involved with neuron differentiation including process formation. The trk receptor-neurotrophin interaction has been found to be more selective than neurotrophin interaction with the p75$^{NGFR}$ receptor. In particular, NGF binds only a trk receptor known as the TrkA receptor, while BDNF, NT-4 and NT-5 exhibit exclusive binding to a TrkB receptor. NT-3 is less selective and, although it binds primarily with a TrkC receptor, it also exhibits some binding to the TrkA and TrkB receptors (Ibanez et al., EMBO J. 1993, 12:2281).

The neurotrophins function primarily to promote survival of certain classes of peripheral and central neurons both during development and following neuronal damage. NGF, in particular, is involved with the development of neurons in the peripheral nervous system and supports neuronal survival, as well as enhancing and maintaining the differentiated state of neurons. However, in some neurological disease states, the neurotrophins may also support inappropriate neurite outgrowth thereby facilitating the progression of a disease condition. For example, neurotrophins promote the undesirable sprouting of hippocampal "mossy fibres". Such inappropriate sprouting of mossy fibres is a common accompaniment of epilepsy in humans. It is also postulated that the pain experienced by patients suffering from some chronic pain syndromes may be associated with sprouting of sensory pain fibers responsive to NGF in particular into the spinal cord. In other pathological states, such as Alzheimer's disease, aberrant process growth, known as dystrophic neurite formation, is a strong correlate of disease severity.

Thus, although the neurotrophins are essential for the normal development and growth of neurons, they may be detrimental under certain circumstances. In such instances, ligands capable of inhibiting or reducing selected neurotrophin-mediated activities would be desirable therapeutically to treat neurodegenerative diseases and conditions including neuropathic pain and to repair nervous system injury.

SUMMARY OF THE INVENTION

It is an object of the present invention to provide compositions capable of inhibiting, or at least reducing, undesirable neurotrophin-mediated activity.

In an aspect of the present invention, a composition is provided which comprises a carrier and an effective amount of a compound of Formula I:

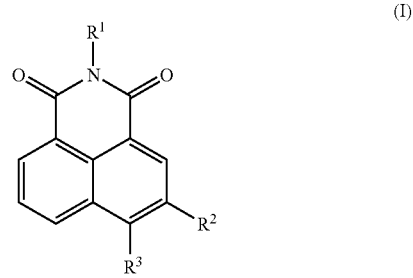

wherein

R$^1$ is selected from alkyl; aryl-loweralkyl; heterocycle-loweralkyl; loweralkyl-carbonate; amino optionally monosubstituted or disubstituted with a substituent selected from loweralkyl, aryl and hydroxyloweralkyl; benzimidaz-2-yl;

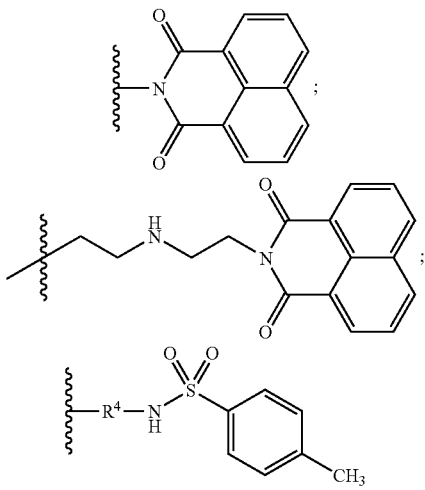

wherein R$^4$ is phenyl optionally monosubstituted or disubstituted with a substituent selected from loweralkyl and halo;

phenyl optionally monosubstituted or disubstituted with a substituent selected from amino, loweralkoxy, hydroxy and loweralkyl; NHCH$_2$CH$_2$OX wherein X represents an in vivo hydrolyzable ester, and loweralkyl-(R$^5$)(R$^6$) wherein one of R$^5$ and R$^6$ is selected from H and loweralkyl and the other is selected from carboxy, carboxy-loweralkyl and loweralkoxycarbonyl; and R$^2$ and R$^3$ are independently selected from H, NO$_2$, halo, di(loweralkyl)amino, cyano, C(O)OH, phenyl-S-, loweralkyl, and Z(O)OR$^7$ wherein Z is selected from C and S and R$^7$ is selected from H, loweralkylamino and arylamino;

and pharmaceutically acceptable salts thereof.

In a further aspect of the present invention, there is provided a method for inhibiting a neurotrophin-mediated activity comprising the step of exposing neurons to a composition as described above.

A further aspect of the present invention provides a method for inhibiting neurotrophin-mediated activity in a mammal comprising the step of administering a composition as described above to said mammal.

These and other aspects of the present invention will be described in greater detail hereinbelow.

DETAILED DESCRIPTION OF THE INVENTION

The term "alkyl" as used herein means straight and branched chain alkyl radicals containing from one to eight carbon atoms and includes methyl, ethyl, propyl, isopropyl, t-butyl pentyl, hexyl, heptyl, octyl and the like.

The term "loweralkyl" as used herein means straight and branched chain alkyl radicals containing from one to four carbon atoms and includes methyl, ethyl, propyl, isopropyl tert-butyl and the like.

The term "alkoxy" as used herein means straight and branched chain alkoxy radicals containing from one to eight carbon atoms and includes methoxy, ethoxy, tert-butoxy and the like.

The term "loweralkoxy" as used herein means straight and branched chain alkoxy radicals containing from one to four carbon atoms and includes methoxy, ethoxy, tert-butoxy and the like.

The term "aryl" as used herein means a 5 or 6 membered aromatic or heteroaromatic ring containing 1, 2 or 3 heteroatoms independently selected from O, N and S, and includes phenyl, pyridyl, thienyl, furanyl pyrrolo, imidazole and the like.

The term "heterocycle" as used herein means a five or six membered, non-aromatic ring optionally containing one or more double bonds and one or two heteroatoms selected from O, S, and N, and includes dihydropyran, tetrahydropyran, tetrahydrofuranyl, azacyclohexane, azacyclohexene, dihydrothiapyran, tetrahydrothiapyran, morpholino and the like.

The term "halo" as used herein means halide and includes fluoro, chloro, bromo and iodo.

As used herein, in vivo hydrolyzable esters or amides are those readily hydrolyzable esters or amides of compounds of Formula I, which are known and used in the pharmaceutical industry and include α-acyloxyalkyl and esters of C$_{3-20}$-fatty acids.

As it is used herein, the term "neurotrophin" refers to neurotrophic factors that are structurally homologous to NGF, i.e. include three surface β-hairpin loops, a β-stand, an internal reverse turn region, and N- and C-termini, and which promote at least one of neuron survival and neuron differentiation, as determined using assays of conventional design such as the in vitro assay exemplified herein and described by Riopelle et al. in Can. J. of Phys. and Pharm., 1982, 60:707. Mammalian nerve growth factor (NGF), brain-derived neurotrophic factor (BDNF), neurotrophin-3 (NT-3), neurotrophin-4 (NT4), neurotrophin-5 (NT-5) and neurotrophin-6 (NT-6) are examples of neurotrophins.

"Neurotrophin-mediated activity" is a biological activity that is normally promoted, either directly or indirectly, in the presence of a neurotrophin. Neurotrophin-mediated activities include, for example, neurotrophin binding to the p75$^{NGFR}$ receptor or neurotrophin binding to one of the trk receptors, neuron survival, neuron differentiation including neuron process formation and neurite outgrowth, and biochemical changes such as enzyme induction. A biological activity that is mediated by a particular neurotrophin, e.g. NGF, is referred to herein by reference to that neurotrophin, e.g. NGF-mediated activity. To determine the ability of a compound to inhibit a neurotrophin-mediated activity, conventional in vitro and in vivo assays can be used. For example, a receptor binding assay, such as the assay described herein in Example 1, can be used to assess the extent to which a compound inhibits neurotrophin/receptor binding. Inhibition of neurite survival and outgrowth can be determined using the i vitro assay described by Riopelle et al. in the Can. J. of Phys. and Pharm., 1982, 60:707, illustrated herein in Example 2.

The present invention relates to compositions comprising an effective amount of a compound of Formula I, or pharmaceutically acceptable salts or in vivo hydrolyzable esters or amides thereof (hereinafter referred to as a compound of Formula I), which inhibits neurotrophin-mediated activity, and a pharmaceutically acceptable carrier.

In embodiments of the invention, compounds of Formula I include those in which R$^1$ is selected from alkyl; aryl-loweralkyl; heterocycle-loweralkyl; loweralkyl-carbonate; amino optionally monosubstituted or disubstituted with a substituent selected from loweralkyl, aryl and hydroxyloweralkyl: benzimidaz-2-yl;

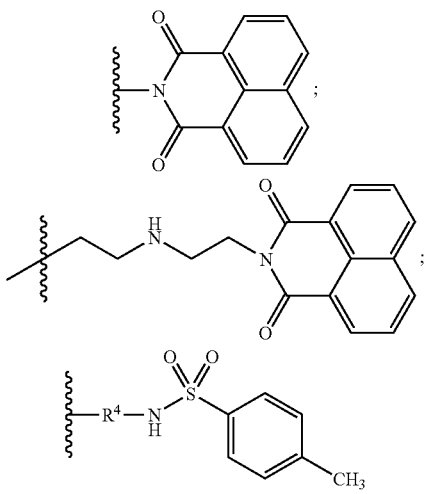

wherein R$^4$ is phenyl optionally monosubstituted or disubstituted with a substituent selected from loweralkyl and halo; phenyl optionally monosubstituted or disubstituted with a substituent selected from amino, loweralkoxy, hydroxy and loweralkyl; NHCH$_2$CH$_2$OX wherein X represents an in vivo hydrolyzable ester, and loweralkyl-$(R^5)(R^6)$ wherein one of $R^5$ and $R^6$ is selected from H and loweralkyl and the other is selected from carboxy, carboxy-loweralkyl and loweralkoxycarbonyl; and $R^2$ and $R^3$ are independently selected from H, $NO_2$, halo, di(loweralkyl)amino, cyano, C(O)OH, phenyl-S-, loweralkyl, and $Z(O)OR^7$ wherein Z is selected from C and S and $R^7$ is selected from H, loweralkylamino and arylamino;

and pharmaceutically acceptable salts thereof.

In another embodiment of the invention, compounds of Formula I include those in which $R^1$ is selected from aryl-loweralkyl; heterocycle-loweralkyl; loweralkyl-carbonate; amino optionally monosubstituted or disubstituted with a substituent selected from loweralkyl and hydroxyloweralkyl; benzimidaz-2-yl; $NHCH_2CH_2OX$ wherein X represents an in vivo hydrolyzable ester; and loweralkyl-$(R^5)(R^6)$ wherein one of $R^5$ and $R^6$ is selected from H and loweralkyl and the other is selected from carboxy, carboxy-loweralkyl and loweralkoxycarbonyl; and $R^2$ and $R^3$ are independently selected from H, $NO_2$, di(loweralkyl)amino, and phenyl-S-; and pharmaceutically acceptable salts thereof.

In a further embodiment of the invention, compounds of Formula I include those in which $R^1$ is selected from amino optionally monosubstituted or disubstituted with a substituent selected from loweralkyl and hydroxyloweralkyl; $NHCH_2CH_2OX$ wherein X represents an in vivo hydrolyzable ester, and loweralkyl-$(R^5)(R^6)$ wherein one of $R^5$ and $R^6$ is selected from H and loweralkyl and the other is selected from carboxy, carboxy-loweralkyl and loweralkoxycarbonyl; and $R^2$ and $R^3$ are independently selected from H and $NO_2$; and pharmaceutically acceptable salts thereof.

In a specific embodiment of the invention, compounds of Formula I include:
- N-{5-Nitro-1H-benz[de]isoquinoline-1,3(2H)-dione}-2-aminoethanol;
- N-Dimethylamino-1,3-dioxo-5-nitro-1,2,3,4-tetrahydrobenzo[i]isoquinoline;
- N-(1,3-Dioxo-5-nitro-1,2,3,4-tetrahydrobenzo[i]isoquinoline)acetic acid;
- N-Acetoxy-1,3-dioxo-1,2,3,4-tetrahydrobenzo[i]isoquinoline;
- N-(1,3-Dioxo-5-nitro-1,2,3,4-tetrahydrobenzo[i]isoquinoline)aminoethanol;
- N-Furfuryl-1,8-naphthalimide;
- 6-(N,N-Dimethylamino)-2-(benzimidazol-2-yl)naphthalimide;
- N-(Pyrid-2-ylethyl)-1,8-naphthalimide;
- 1,3-Dioxo-6-phenylmercapto-N-(pyrid-2-ylethyl)-1,2,3,4-tetrahydrobenzo[i]isoquinoline;
- 2-{2-(4-Methylphenylsulphonamido)phenyl}-6-(N,N-dimethylamino) naphthalimide;
- 1,3-Dioxo-2-{2-(4-methylphenylsulphonamido)phenyl}-1,2,3,4-tetrahydrobenzo[i]isoquinoline;
- N-Octyl-5-nitronaphthalimide;
- 5-Bromo-1,3-dioxo-N-methylpyrid-3-yl-1,2,3,4-tetrahydrobenzo-[i]isoquinoline;
- 1,3-Dioxo-5-nitro-N-(pyrid-2-ylethyl)-1,2,3,4tetrahydrobenzo[i]isoquinoline;
- 6-Nitro-2-(tetrahydrofuran-2-ylmethyl)naphthalimide;
- N-(1,3-Dioxo-1,2,3,4-tetrahydrobenzo[i]isoquinoline)aminoethanol;
- Naphthalicacid-N-aminoimide;
- 2-{2-(4-Methylbenzsulphonamido)-4,5-dichlorophenyl}naphthalimide;
- 3-Nitro-1,8-(N-propioncarboxylate)succinamidonapthalene;
- 1,3-Dioxo-2-(2-aminophenyl)-1,2,3,4-tetrahydrobenzo[i]isoquinoline;
- 6-Nitro-2-(pyrid-3-methyl)naphthalimide;
- 3-Amino-7,4-bis(ethyl-1,3-dioxo)-1,2,3,4-tetrahydrobenzo[i]isoquinoline;
- 2-(Benzimidaz-2-yl)-1,3-dioxo-1,2,3,4-tetrahydrobenzo[i]isoquinoline;
- 2-(2-Aminophenyl)naphthalimide;
- 1,3-Dioxo-2-{4,5-dimethyl-2-(4-methylphenylsulphonamido)phenyl}-1,2,3,4-tetrahydrobenzo[i]isoquinoline;
- 3-Methyl-3-(1,3-dioxo-5-nitro(1H,3H)benz[de]isoquinolyl)butyric acid methylester;
- 1,3-Dioxo-N-methyltetrahydrofurfur-2-yl-5-nitro-1,2,3,4-tetrahydro-[i]isoquinoline;
- N-(4-Ethoxyphenyl)-5-nitronaphthalimide;
- 6-Nitro-2-(furfuryl)naphthalimide;
- Ethyl-5-nitro-1,3-dioxo-1H-benz[de]isoquinoline-2-3H-acetate;
- Naphthalicacid-N,N'-diimide;
- 2-(2-Hydroxyphenyl)naphthalimide;
- 5-Amino-N-butylnaphthalimide;
- 1,3-Dioxo-5-nitro-n-propylmorpholino-1,2,3,4-tetrahydrobenzo-[i]isoquinoline;
- 6-Nitro-2-(pyrid-2-ylethyl)naphthalimide;
- N-Methylnaphthalimide;
- N(Pyrid-2-ylmethyl)naphthalimide;
- N-(3,5-Dimethylphenyl)-1,8-naphthalimide;
- 6-Bromo-N-dimethylamino-1,3-dioxo-1,2,3,4-tetrahydrobenzo-[i]isoquinoline;
- N-(1,3-Dioxo-6-phenylmercapto-1,2,3,4-tetrahydrobenzo[i]isoquinoline)-aminoethanol; and
- N-Anilino-1,8-naphthalimide.

In a preferred embodiment of the invention, compounds of Formula I include:
- N-{5-Nitro-1H-benz[de]isoquinoline-1,3(2H)-dione}-2-aminoethanol;
- N-Dimethylamino-1,3-dioxo-5-nitro-1,2,3,4tetrahydrobenzo[i]isoquinoline;
- N-(1,3-Dioxo-5-nitro-1,2,3,4-tetrahydrobenzo[i]isoquinoline)acetic acid;
- N-Acetoxy-1,3-dioxo-1,2,3,4-tetrahydrobenzo[i]isoquinoline;
- N-(1,3-Dioxo-5-nitro-1,2,3,4-tetrahydrobenzo[i]isoquinoline)aminoethanol;
- N-Furfuryl-1,8-naphthalimide;
- 6-(N,N-Dimethylamino)-2-(benzimidazol-2-yl)naphthalimide;
- N-(Pyrid-2-ylethyl)-1,8-naphthalimide;
- 1,3-Dioxo-6-phenylmercapto-N-(pyrid-2-ylethyl)-1,2,3,4-tetrahydrobenzo[i]isoquinoline;
- 2-{2-(4-Methylphenylsulphonamido)phenyl}-6-(N,N-dimethylamino) naphthalimide;
- 1,3-Dioxo-2-{2-(4-methylphenylsulphonamido)phenyl}-1,2,3,4-tetrahydrobenzo[i]isoquinoline;
- N-Octyl-5-nitronaphthalimide;
- 5-Bromo-1,3-dioxo-N-methylpyrid-3-yl-1,2,3,4-tetrahydrobenzo-[i]isoquinoline;
- 1,3-Dioxo-5-nitro-N-(pyrid-2-ylethyl)-1,2,3,4tetrahydrobenzo[i]isoquinoline;
- 6-Nitro-2-(tetrahydrofuran-2-ylmethyl)naphthalimide;
- N-(1,3-Dioxo-1,2,3,4-tetrahydrobenzo[i]isoquinoline) aminoethanol;
- Naphthalicacid-N-aminoimide;
- 2-{2-(4-Methylbenzsulphonamido)-4,5-dichlorophenyl}naphthalimide;
- 3-Nitro-1,8-(N-propioncarboxylate)succinamidonapthalene;

1,3-Dioxo-2-(2-aminophenyl)-1,2,3,4-tetrahydrobenzo[i]
isoquinoline;
6-Nitro-2-(pyrid-3-methyl)naphthalimide;
3-Amino-7,4-bis(ethyl-1,3-dioxo)-1,2,3,4-tetrahy-
drobenzo[i]isoquinoline;
2-(Benzimidaz-2-yl)-1,3-dioxo-1,2,3,4-tetrahydrobenzo
[i]isoquinoline; and
2-(2-Aminophenyl)naphthalimide;

In a more preferred embodiment of the invention, compounds of Formula I include:
N-{5-Nitro-1H-benz[de]isoquinoline-1,3(2H)-dione}-2-
aminoethanol;
N-Dimethylamino-1,3-dioxo-5-nitro-1,2,3,4-tetrahy-
drobenzo[i]isoquinoline;
N-(1,3-Dioxo-5-nitro-1,2,3,4-tetrahydrobenzo[i]iso-
quinoline)acetic acid;
N-Acetoxy-1,3-dioxo-1,2,3,4-tetrahydrobenzo[i]iso-
quinoline;
N-(1,3-Dioxo-5-nitro-1,2,3,4-tetrahydrobenzo[i]iso-
quinoline)aminoethanol;
N-Furfuryl-1,8-naphthalimide;
6-(N,N-Dimethylamino)-2-(benzimidazol-2-yl)naphthal-
imide;
N-(Pyrid-2-ylethyl)-1,8-naphthalimide; and
1,3-Dioxo-6-phenylmercapto-N-(pyrid-2-ylethyl)-1,2,3,
4-tetrahydrobenzo[i]isoquinoline.

In a most preferred embodiment of the invention, compounds of Formula I include:
N-{5-Nitro-1H-benz[de]isoquinoline-1,3(2H)-dione}-2-
aminoethanol;
N-Dimethylamino-1,3-dioxo-5-nitro-1,2,3,4-tetrahy-
drobenzo[i]isoquinoline;
N-(1,3-Dioxo-5-nitro-1,2,3,4-tetrahydrobenzo[i]iso-
quinoline)acetic acid;
N-Acetoxy-1,3-dioxo-1,2,3,4-tetrahydrobenzo[i]iso-
quinoline; and
N-(1,3-Dioxo-5-nitro-1,2,3,4-tetrahydrobenzo[i]iso-
quinoline)aminoethanol.

Another embodiment of the invention includes an in vivo hydrolyzable ester or amide of a compound selected from the group consisting of:
N-{5-Nitro-1H-benz[de]isoquinoline-1,3(2H)-dione}-2-
aminoethanol;
N-(1,3-Dioxo-5-nitro-1,2,3,4-tetrahydrobenzo[i]iso-
quinoline)acetic acid;
N-(1,3-Dioxo-5-nitro-1,2,3,4-tetrahydrobenzo[i]iso-
quinoline)aminoethanol;
N-(1,3-Dioxo-1,2,3,4-tetrahydrobenzo[i]isoquinoline)
aminoethanol;
Naphthalicacid-N-aminoimide;
3-Nitro-1,8-(N-propioncarboxylate)succinamidonaptha-
lene;
1,3-Dioxo-2-(2-aminophenyl)-1,2,3,4-tetrahydrobenzo[i]
isoquinoline;
3-Amino-7,4-bis(ethyl-1,3-dioxo)-1,2,3,4-tetrahy-
drobenzo[i]isoquinoline;
2-(2-Aminophenyl)naphthalimide; and
2-(2-Hydroxyphenyl)naphthalimide.

The compounds of the present invention can be prepared by techniques well known in the art Compounds of formula I wherein $R^1$, $R^2$ and $R^3$ are as defined above can be prepared by reacting a 1,8-naphthalic anhydride of Formula A with a primary amine of Formula B in a suitable solvent such as toluene, methanol, ethanol, propanol or acetone and at temperatures in the range of 0° C. to the boiling point of the solvent used. Both reagent A and reagent B are commercially available or can be prepared using procedures known to one skilled in the art.

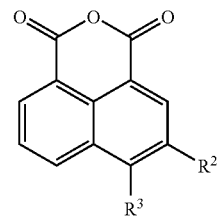

Acid addition salts of the compounds of Formula I are most suitably formed from pharmaceutically acceptable acids, and include for example those formed with inorganic acids e.g hydrochloric, sulphuric or phosphoric acids and organic acids e.g. succinic, maleic, acetic or fumaric acid. Other non-pharmaceutically acceptable salts e.g. oxalates may be used for example in the isolation of the compound of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

In vivo hydrolyzable esters or amides of certain compounds of Formula I can be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of Formula 1 having a free carboxy group may be esterified using standard conditions which may include activation followed by treatment with the desired alcohol in the presence of a suitable base.

The compositions of the present invention are useful to inhibit or reduce undesirable neurotrophin activity both in vitro and in vivo. Thus, in an aspect of the invention, a composition comprising an effective amount of a compound of Formula I and a suitable carrier is provided. By "suitable carrier" is meant a carrier which admixes with the compound of Formula I to yield a composition suitable for the application for which it is to be used. By "effective amount" is meant an amount of the compound sufficient to inhibit an undesired neurotrophin-mediated activity to a measurable extent, preferably by about 20%, more preferably by about 40%, most preferably by about 50%, as determined using assays of conventional design such as those described herein in the specific examples.

The present composition has use as a media supplement to prevent undesirable neurotrophin-mediated activity of neuron cells in vitro. For example, primary sensory neurons require NGF for survival in cell culture; however, NGF also influences neuron differentiation, notably process formation and outgrowth, which are undesirable for the use of primary sensory neurons in cell culture. Thus, to preserve neuron survival in vitro while inhibiting cell differentiation, NGF is added to the cell culture media along with the compound of Formula I. For addition to the cell culture, the compound is first combined with a carrier which will not adversely affect the growth of the cells in culture. Such carriers will include, for example, physiologically acceptable fluids such as water or any other fluid suitable for addition to the cell culture. Alternatively, the compound can be combined with media suitable for culturing neuronal cells prior to being added to the cell culture. To be effective to prevent neuron differentiation, the concentration of the compound in the cell culture will be in the range of from about 1-500 µM, and preferably from about 1-100 µM. The optimal concentration of compound for use in preventing neuron differentiation in cell culture will, of course, vary depending on the extent of inhibition desired as well as the type of neuronal cells involved.

Compositions for in vivo administration, e.g. for treating neurological conditions such as epilepsy or Alzheimer's disease, or for treating chronic pain, are also contemplated. Such compositions comprise a therapeutically effective amount of the compound of Formula I together with a pharmaceutically acceptable carrier. In this context, the term "pharmaceutically acceptable" means acceptable for use in the pharmaceutical and veterinary arts, i.e. non-toxic and not adversely affecting the activity of the compound. The term "therapeutically effective amount" means an amount of the compound sufficient to reduce undesirable neurotrophin-mediated activity, as determined using assays of conventional design, in an inflicted individual without causing adverse effects.

Pharmaceutically acceptable carriers useful to prepare compositions for in vivo administration include conventional carriers used in formulating drugs, such as diluents, excipients and the like. Reference may be made to "Remington's Pharmaceutical Sciences", 17th Ed., Mack Publishing Company, Easton, Pa., 1985, for guidance on drug formulations generally. As will be appreciated, the pharmaceutical carriers used to prepare compositions in accordance with the present invention will depend on the dosage form to be used to treat the inflicted individual.

According to one embodiment of the invention, a compound of Formula I is formulated for administration by injection intraventricularly, and is accordingly provided as an aqueous solution in sterile and pyrogen-free form and optionally buffered or made isotonic. Thus, the compound may be administered in distilled water or, more desirably, in saline or 5% dextrose solution. Water solubility of the compound of the invention may be enhanced, if desired, by incorporating into the composition a solubility enhancer, such as acetyltrimethylammonium bromide or chloride. Lyoprotectants, such as mannitol, sucrose or lactose and buffer systems, such as acetate, citrate and phosphate may also be included in the formulation, as may bulking agents such as serum albumin.

For use in treating individuals with a neurological condition, precise dosage sizes of a pharmaceutical composition appropriate for treatment are established in appropriately controlled trials, and will correspond to an amount of a compound of Formula I that reduces undesirable neurotrophin-mediated activity without causing intolerable side effects to the individual being treated. It is anticipated that an effective treatment regimen for patients will involve the intraventricular administration of dosages which achieve a level of the compound in the spinal fluid of the individual being treated of about 1-500 µM. It will be appreciated, of course, that the dosage sizes required to attain this in vivo concentration will vary according to the route of administration, the frequency of administration, on the individual being treated and on the neurological condition being treated.

Specific embodiments of the present invention are described in more detail in the following examples which are not to be construed as limiting.

EXAMPLE 1

Binding of [$^{125}$I]NGF to PC12 cells in the presence and absence of BDNF

The ability of the compounds of Formula I to antagonize NGF interaction with the p75 and trkA receptors was determined as follows.

(A) Iodination of NGF

NGF was labelled using the Lactoperoxidase labelling method (Sutter et al., *J. Biol. Chem.*, 1979) and the labelled NGF was separated from radiolabelling agents and free iodide using a PD-10 Sephadex G-25 column.

(B) Cell Culture and Cell Preparation

PC12 cells were grown in RPMI with 10% heat inactivated donor horse serum and 5% fetal calf serum. Cells were harvested for binding by washing off the media with calcium-magnesium free balanced salt solution (Gey's solution) and incubated in 5 ml Gey's solution at 37° C. for 15 minutes. Cells were pelleted by centrifugation and suspended in Hepes-Krebs Ringer buffer (HKR) (10 mM Hepes pH7.35, containing 125 mM NaCl, 4.8 mM KCl, 1.3 mM $CaCl_2$, 1.2 mM $MgSO_4$, 1.2 mM $KH_2PO_4$, 1 mg/ml BSA and 1.0 mg/ml glucose) at a concentration of $4\times10^6$/ml and kept on ice.

(C) NGF Binding

The reaction was performed in a 96 well plate. Suspended cells (150 ul, $10^6$ cells) were added to $^{125}$I-NGF (final concentration of 0.5 nM) and the competing compound of Formual I in a final volume of 300 ul of HKR buffer. The plates were incubated with shaking for 2 hr at 4° C. At the end of the incubation, 100 ul aliquots of the reaction sample were added to 400 ul microcentrifuge tubes containing 200 ul of 10% glycerol in HKR buffer. The tubes were centrifuged for 1 minute at ~5000 rpm and the tip containing the cell pellet was cut off. Radioactivity bound to the cells was determined by measuring the $^{125}$I-NGF associated with each pellet in a gamma counter. Specific binding is calculated as the difference between the amount of $^{125}$I-NGF bound in the absence (total) and presence (NSB) of 50 nM unlabeled NGF. TrkA binding is determined similarly except 10 nM BDNF is added to all reactions. Table 1 summarizes the values obtained from this experiment for the inhibition of binding of NGF to P75 and TrkA by compounds of Formula I.

TABLE 1

| Compound | % Inhibition at 100 uM |
| --- | --- |
| N-Dimethylamino-1,3-dioxo-5-nitro-1,2,3,4-tetrahydrobenzo[i]isoquinoline | 59 |
| N-(1,3-Dioxo-5-nitro-1,2,3,4-tetrahydrobenzo[i]isoquinoline)acetic acid | 58 |

TABLE 1-continued

| Compound | % Inhibition at 100 uM |
|---|---|
| N-Acetoxy-1,3-dioxo-1,2,3,4-tetrahydrobenzo[i]isoquinoline | 57 |
| N-(1,3-Dioxo-5-nitro-1,2,3,4-tetrahydrobenzo[i]isoquinoline)-aminoethanol | 44 |
| N-Furfuryl-1,8-naphthalimide | 36 |
| 6-(N,N-Dimethylamino)-2-(benzimidazol-2-yl)naphthalimide | 36 |
| N-(Pyrid-2-ylethyl)-1,8-naphthalimide | 35 |
| 1,3-Dioxo-6-phenylmercapto-N-(pyrid-2-ylethyl)-1,2,3,4-tetrahydro-benzo[i]isoquinoline | 33 |
| 2-{2-(4-methylphenylsulphonamido)phenyl}-6-(N,N-dimethylamino)-naphthalimide | 29 |
| 1,3-Dioxo-2-{2-(4-methylphenylsulphonamido)phenyl}-1,2,3,4-tetrahydrobenzo[i]isoquinoline | 29 |
| N-Octyl-5-nitronaphthalimide | 29 |
| 5-Bromo-1,3-dioxo-N-methylpyrid-3-yl-1,2,3,4-tetrahydrobenzo[i]isoquinoline | 28 |
| 1,3-Dioxo-5-nitro-N-(pyrid-2-ylethyl)-1,2,3,4-tetrahydrobenzo[i]isoquinoline | 28 |
| 6-Nitro-2-(tetrahydrofuran-2-ylmethyl)naphthalimide | 28 |
| N-(1,3-Dioxo-1,2,3,4-tetrahydrobenzo[i]isoquinoline)aminoethanol | 27 |
| Naphthalicacid-N-aminoimide | 27 |
| 2-[2-(4-Methylbenzsulphonamido)-4,5-dichlorophenyl]naphthalimide | 26 |
| 3-Nitro-1,8-(N-propioncarboxylate)succinamidonapthalene | 25 |
| 1,3-Dioxo-2-(2-aminophenyl)-1,2,3,4-tetrahydrobenzo[i]isoquinoline | 24 |
| 6-Nitro-2-(pyrid-3-methyl)naphthalimide | 23 |
| 3-Amino-7,4-bis(ethyl-1,3-dioxo-1,2,3,4-tetrahydrobenzo[i]isoquinoline | 23 |
| 2-(Benzimidaz-2-yl)-1,3-dioxo-1,2,3,4-tetrahydrobenzo[i]isoquinoline | 23 |
| 2-(2-Aminophenyl)naphthalimide | 20 |
| 1,3-Dioxo-2-[4,5-dimethyl-2-(4-methylphenylsulphonamido)phenyl]-1,2,3,4-tetrahydrobenzo[i]isoquinoline | 19 |
| N-(4-Ethoxyphenyl)-5-nitronaphthalimide | 18 |
| 1,3-Dioxo-N-methyltetrahydrofurfur-2-yl-5-nitro-1,2,3,4-tetrahydro[i]isoquinoline | 18 |
| 3-Methyl-3-(1,3-dioxo-5-nitro(1H,3H)benz[de]isoquinolyl)butyric acid methylester | 17 |
| 6-Nitro-2-(furfuryl)naphthalimide | 17 |
| Ethyl-5-nitro-1,3-dioxo-1H-benz[de]isoquinoline-2-3H-acetate | 16 |
| Naphthalicacid-N,N'-diimide | 13 |
| 2-(2-Hydroxyphenyl)naphthalimide | 13 |
| 5-Amino-N-butylnaphthalimide | 13 |
| 1,3-Dioxo-5-nitro-n-propylmorpholino-1,2,3,4-tetrahydrobenzo[i]isoquinoline | 11 |
| 6-Nitro-2-(pyrid-2-ylethyl)naphthalimide | 11 |
| N-Methylnaphthalimide | 11 |
| N-(Pyrid-2-ylmethyl)naphthalimide | 10 |
| N-(3,5-Dimethylphenyl)-1,8-naphthalimide | 9 |
| 6-Bromo-N-dimethylamino-1,3-dioxo-1,2,3,4-tetrahydrobenzo[i]-isoquinoline | 5 |
| N-(1,3-Dioxo-6-phenylmercapto-1,2,3,4-tetrahydrobenzo[i]isoquinoline)aminoethanol | 3 |
| N-Anilino-1,8-naphthalimide | 1 |

EXAMPLE 2

Inhibition of Neurite Outgrowth

The ability of N-{5-nitro-1H-benz[de]isoquinoline-1,3(2H)-dione}-2-aminoethanol (Compound A) to inhibit neurite outgrowth was determined using the following assay.

Eight-day chick embryo dorsal root ganglia (DRG) were freed of meninges and removed aseptically. The DRG were kept at 4° C. at all times. Ganglia from six embryos (40-50 per embryo) were washed in $Ca^{2+}$- and $Mg^{2+}$-free Gey's balanced salt solution (Gibco) and exposed to 0.01% trypsin (Worthington) in the same solution for 10 min at 37° C. A half-volume of phosphate-buffered Gey's balanced salt solution was added for a further 5 min at 37° C. and the reaction was then terminated with one-third volume of Ham's F12 medium (Gibco) containing 5% fetal calf serum (FCS, Gibco). The ganglia were then triturated using a 5 mL narrow-tip pipette to a single cell suspension. Following filtration through 37-mm nylon mesh (Small Parts Inc., Miami, Fla.) in a Millipore chamber to remove clumps, the cell suspension was washed through a 500-ml FCS undercut (700×g for 5 min at 4° C.) and resuspended in 4 mL of Ham's F12 medium plus 5% FCS. The cell suspension was then preplated on a 100-mm Flacon culture dish and incubated for 45-60 min at 37° C. in a 5% $CO_2$ humidified atmosphere. Cells enriched in neurons were decanted for the bioassay, since non-neuronal cells of DRG preferentially stick to the culture substrate.

The inside wells of 96-well Falcon microculture plates were coated with polylysine (0.1 mg/mL) (Sigma) for 4 h at 37° C. (the outside wells were filled with distilled water to provide humidity) and, following a rinse with tissue culture media, 100 mL of neuron-rich cell suspension was added to each well at $10^5$ cells/mL. Ninety (90) mL of NGF solution (prepared in tissue culture media) was then added to each well to a final concentration of 0.25 ng/mL NGF per well. Ten (10) mL of test compound solution, i.e. tissue culture media admixed with a compound of Formula I, was then added to test wells in duplicate to yield wells containing compound concentrations ranging from 0 μM-100 μM. For control assays, 10 mL of Ham's F12 medium was added to duplicate NGF-containing wells. The plates were covered and incubated in the dark for 24-30 hrs. at 37° C. in a 5% $CO_2$ humidified atmosphere.

The bioassays were read using a Leitz Diavert microscope with phase optics. To afford adequate optics, the meniscus effect of each well was removed by filling the well with a balanced salt solution until a flat, air-filled interface was achieved at the top of the well. At least 100 neurons per well were counted, and the assay was scored as the ratio of cells bearing neurites greater than one cell diameter to total viable (phase bright) cells. These results are summarized in Table 2.

TABLE 2

| Group | Ratio | Std Dev | SEM |
|---|---|---|---|
| NGF Control | 1.000 | 0.16 | 0.06 |
| 5 μM Compound A | 1.1 | 0.42 | 0.15 |
| 50 μM Compound A | 0.16 | 0.15 | 0.05 |
| 100 μM Compound A | 0.016 | 0.02 | 0.01 |

EXAMPLE 3

Animal Models of Neuropathic Pain

For pain related to nerve injury, the compound N-{5-nitro-1H-benz[de]isoquinoline-1,3(2H)-dione}-2-aminoethanol (Compound A) was tested in nerve-ligated rats for activity against tactile allodynia, thermal hyperalgesia and in direct production of thermal antinociception The nerve-ligation model is commonly accepted as representing aspects of neuropathic pain reported by humans. Sham operated rats served as appropriate controls for the neuropathic experiments.

Nerve Ligation Injury:

Nerve ligation injury was performed according to the method described by Kim and Chung (Pain 50: 355-363, 1992). Rats were anesthetized with halothane and the vertebrae over the L4 to S2 region were exposed. L5 and L6 spinal nerves were exposed, carefully isolated, tightly ligated with 4-0 silk suture distal to the DRG. After ensuring homeostatic stability, the wounds were sutured, and the animals were allowed to recover in the cages. Sham-operated rats were prepared in an identical fashion except that the L5/L6 nerve roots are not ligated.

Intrathecal Catheter Placement:

The test compounds were injected through indwelling i.th. catheters. While under anesthesia, PE-10 tubing (8 cm) was inserted through an incision made in the atlanto-occipital membrane to the level of the lumbar enlargement of the rat and secured. Drug injections were made in a volume of 5 µl of 50% aqueous DMSO followed by a 9 µl saline flush.

Endpoints:

(A) Evaluation of Tactile Allodynia:

Mechanical alloydynia was determined in the manner described by Chaplan et al. (J. Neurosci. Meth. 53:55-63, 1994). The paw withdrawal threshold was determined in response to probing with calibrated von Frey filaments. The rats were kept in suspended cages with mesh floors and the von Frey filaments were applied perpendicularly to the plantar surface of the paw of the rat until it buckled slightly, and held for 3-6 sec. A positive response was indicated by a sharp withdrawal of the paw. The 50% paw withdrawal threshold was determined by the non-parametric method of Dixon (Ann. rev. Pharmacol. Toxicol. 20: 441-462, 1980).

(B) Evaluation of Thermal Hyperalgesia:

Thermal hyperalgesia was determined by focusing a radiant heat source onto the plantar surface of the affected paw of nerve-injured or sham-operated rats. Paw withdrawal latencies are determined by a photodetection device which halts the stimulus and the timer after a maximum cut-off of 40 sec to prevent tissue damage. The withdrawal latency of sham-operated rats were compared to those of ligated rats to measure the degree of hyperalgesia.

(C) Evaluation of Acute Nociceptive Responses:

Acute nociception was determined by using the nociceptive warm water tail-flick reflex. This test was performed by placing the tail of the nerve-injured or sham-operated rats in a heated water bath maintained at 55° C. The latency until tail withdrawal (rapid flick) from the bath was determined and compared among treatments. A 15 second cut-off was employed to avoid tissue damage.

Compound A and morphine were tested in the nerve-ligated injury model of neuropathic pain using 3 routes of administration: intrapertoneally (i.p.), intra-thecally (i.th.) and intracerebroventrically (i.c.v.). The compounds were evaluated for three endpoints: tactile allodynia, thermal hyperalgesia and acute nociception. Compound A is not active when given i.c.v. The results for i.p and i.th. administration are shown in Table 3.

TABLE 3

Summary of the $A_{50}$ doses with 95% Confidence Limits (C.L.) for Compound A and Morphine in L5/L6 Nerve Ligated and Sham-Operated Rats in Models of Tactile Allodynia, Acute Nociception and Thermal Hyperalgesia

| Treatment | | Compound A $A_{50}$(95% C.L.) | Morphine $A_{50}$(95% C.L.) |
|---|---|---|---|
| Allodynia- Ligated | i.th | 34.6 µg | >100 µg |
| | i.p. | 38 mg/kg | 7.1 mg/kg |
| Tail Flick- Ligated | i.th | 78 µg | 2.3 µg |
| | i.p. | 27.8 mg/kg | na* |
| Tail Flick- Sham | i.th | 34 µg | 1.45 µg |
| | i.p. | 25.7 mg/kg | na |
| Hot Plate- Ligated | i.th | 14.8 µg | na |
| | i.p. | 18.6 mg/kg | na |
| Hot Plate- Sham | i.th | 48.1 µg | na |
| | i.p. | 34.9 mg/kg | na |

*na = not available

EXAMPLE 4

Preparation of N-{5-nitro-1H-benz[de]isoquinoline-1,3(2H)-dione}-2-aminoethanol (Compound A)

3-Nitro-1,8-naphthalic anhydride (1 eq) and 2-hydroxyethylhydrazine (1 eq) are dissolved in toluene and heated to reflux. The reaction is monitored by tlc and halted when all of the starting materials are consumed. The solvent is removed under reduced pressure and the product purified, if necessary, by recrystallization or silica gel chromatography.

Other compounds of Formula I can be prepared in an analogous manner, or are available commercially from Ryan Scientific Inc., Isle of Palms, S.C., U.S.

We claim:

1. A method of treating pain in a mammal comprising the step of administering to said mammal a therapeutically effective amount of a pharmaceutical composition comprising a compound of Formula I:

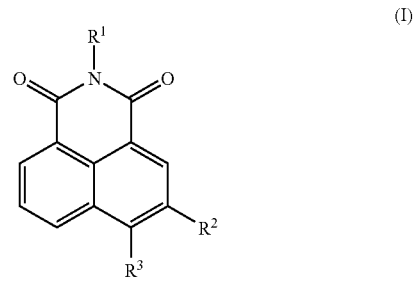

(I)

wherein:
 $R^1$ is selected from the group consisting of: amino optionally monosubstituted or disubstituted with $C_1$-$C_4$ alkyl or hydroxy($C_1$-$C_4$ alkyl); and $C_1$-$C_4$ alkyl-($R^5$)($R^6$) wherein one of $R^5$ and $R^6$ is selected from H and $C_1$-$C_4$ alkyl, and the other is selected from carboxy, carboxy-($C_1$-$C_4$ alkyl) and ($C_1$-$C_4$ alkoxy)-carbonyl; and
 $R^2$ and $R^3$ are independently selected from H and $NO_2$.

* * * * *